(12) United States Patent
Lown

(10) Patent No.: US 11,974,769 B2
(45) Date of Patent: *May 7, 2024

(54) CARPAL TUNNEL RELEASE SYSTEMS AND METHODS

(71) Applicant: EDGE INSTRUMENTS, LLC, Austin, TX (US)

(72) Inventor: Ira Lown, Austin, TX (US)

(73) Assignee: EDGE INSTRUMENTS, LLC, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/836,514

(22) Filed: Jun. 9, 2022

(65) Prior Publication Data

US 2022/0296269 A1    Sep. 22, 2022

Related U.S. Application Data

(63) Continuation of application No. 16/703,282, filed on Dec. 4, 2019, now Pat. No. 11,357,531, which is a continuation of application No. 15/440,808, filed on Feb. 23, 2017, now Pat. No. 10,499,942.

(60) Provisional application No. 62/299,176, filed on Feb. 24, 2016.

(51) Int. Cl.
*A61B 17/32* (2006.01)

(52) U.S. Cl.
CPC .............. *A61B 17/320036* (2013.01)

(58) Field of Classification Search
CPC .... A61B 17/320016; A61B 17/320036; A61B 17/320783
See application file for complete search history.

(56) References Cited

U.S. PATENT DOCUMENTS

| | | |
|---|---|---|
| 4,962,770 A | 10/1990 | Agee et al. |
| 4,963,147 A | 10/1990 | Agee et al. |
| 5,089,000 A | 2/1992 | Agee et al. |
| 5,273,024 A | 12/1993 | Menon et al. |
| 5,306,284 A | 4/1994 | Agee et al. |
| 5,431,153 A | 7/1995 | Lee |
| 5,507,800 A | 4/1996 | Strickland |

(Continued)

FOREIGN PATENT DOCUMENTS

DE    102009030254 A1    12/2010

OTHER PUBLICATIONS

Arthrex, "Centerline™ Endoscopic Carpal Tunnel Release System," www.arthrex.com, 2015, 3 pages.

(Continued)

*Primary Examiner* — Ryan J. Severson
(74) *Attorney, Agent, or Firm* — Trop, Pruner & Hu, P.C.

(57) ABSTRACT

An embodiment includes an apparatus for carpel tunnel syndrome surgery. The apparatus comprises: a shaft including a shaft proximal end, a shaft distal end, and a shaft long axis, wherein the shaft distal end comprises a raised edge; a linkage included within the shaft; a blade coupled to a distal end of the linkage; wherein (a)(i) an axis parallel to the shaft long axis intersects the raised edge but does not intersect the shaft, (a)(ii) the raised edge is curvilinear, (a)(iii) the raised edge includes a first lateral edge portion, a second lateral edge portion, and a middle edge portion between the first and second lateral edge portions; and (a)(iv) the first and second lateral edge portions are both proximal to the middle edge portion. Other embodiments are described herein.

20 Claims, 12 Drawing Sheets

(56) References Cited

U.S. PATENT DOCUMENTS

| | | |
|---|---|---|
| 5,586,990 A | 12/1996 | Hahnen et al. |
| 5,730,749 A | 3/1998 | Battenfield |
| 5,827,311 A | 10/1998 | Berelsman et al. |
| 6,139,489 A | 10/2000 | Wampler et al. |
| 6,685,717 B1 | 2/2004 | Ilic |
| 7,628,798 B1 | 12/2009 | Welborn |
| 7,918,784 B2 | 4/2011 | Welborn et al. |
| 8,257,379 B2 | 9/2012 | Lee |
| 8,303,594 B2 | 11/2012 | Lynch et al. |
| 8,348,966 B2 | 1/2013 | McCormack et al. |
| 8,523,865 B2 | 9/2013 | Reglos et al. |
| 8,523,891 B2 | 9/2013 | Welborn |
| 8,523,892 B2 | 9/2013 | Rehnke et al. |
| 8,551,129 B2 | 10/2013 | Lary et al. |
| 8,591,514 B2 | 11/2013 | Sherman |
| 8,608,763 B1 | 12/2013 | Jurbala |
| 8,608,765 B1 | 12/2013 | Jurbala |
| 8,771,304 B1 | 7/2014 | Jurbala |
| 8,827,893 B2 | 9/2014 | Mirza et al. |
| 8,840,631 B2 | 9/2014 | Messmer |
| 8,951,273 B1 | 2/2015 | Fard |
| 8,992,424 B2 | 3/2015 | Orbay et al. |
| 9,642,643 B1 | 5/2017 | Jurbala |
| 10,499,942 B2 | 12/2019 | Lown |
| 2007/0112366 A1 | 5/2007 | Welborn et al. |
| 2007/0123889 A1 | 5/2007 | Malandain et al. |
| 2008/0045989 A1 | 2/2008 | Welborn |
| 2008/0195128 A1 | 8/2008 | Orbay et al. |
| 2008/0200758 A1 | 8/2008 | Orbay et al. |
| 2009/0125044 A1 | 5/2009 | Lary |
| 2009/0125047 A1 | 5/2009 | Reglos et al. |
| 2010/0168750 A1 | 7/2010 | Sherman |
| 2010/0228275 A1 | 9/2010 | Welborn |
| 2011/0046652 A1 | 2/2011 | Rehnke et al. |
| 2011/0098709 A1 | 4/2011 | Malandain et al. |
| 2011/0201881 A1 | 8/2011 | Emch |
| 2012/0029542 A1 | 2/2012 | Huang |
| 2012/0029543 A1 | 2/2012 | Lee |
| 2012/0150208 A1 | 6/2012 | Messmer |
| 2013/0144318 A1 | 6/2013 | Dinis Carmo |
| 2014/0171790 A1 | 6/2014 | Guo |
| 2017/0238958 A1 | 8/2017 | Lown |
| 2020/0100806 A1 | 4/2020 | Lown |

OTHER PUBLICATIONS

Hamed et al. "Carpal Tunnel Release via Mini-Open Wrist Crease Incision: Procedure and Results of Four Years Clinical Experience," Pakistan Journal of Medical Sciences, Oct.-Dec. 2006; vol. 22 (4), 9 pages.

Kim et al. "Current Approaches for Carpal Tunnel Syndrome," Clinics in Orthopedic Surgery, KoreaMed Synapse, v.6 (3), Sep. 2014, 5 pages.

Warhold et al. "Endoscopic carpal tunnel decompression," Pb Journal of Orthopaedics vol. XIII, No. 1, 2012, 15 pages.

"SmartRelease™ Endoscopic Carpal Tunnel Release ECTR", MicroAire Surgical Instruments, 2011, 16 pages.

Product Listing, "KnifeLight," www.whichmedicaldevice.com, Manufacturer: Stryker, Jan. 9, 2012, 2 pages.

McCormack, "Carpal Tunnel Release Using the MANOS CTR System," Carpal Tunnel Syndrome, University of California, San Francisco, Nova Science Publishers, Inc., © 2014, ISBN: 978-1-63321-142-1, 18 pages.

Newsletter, "Arthroscopic Biceps Tenodesis," Scope This Out: A Technical Pearls Newsletter for Arthroscopists, vol. 12, No. 2, Fall 2010, 8 pages.

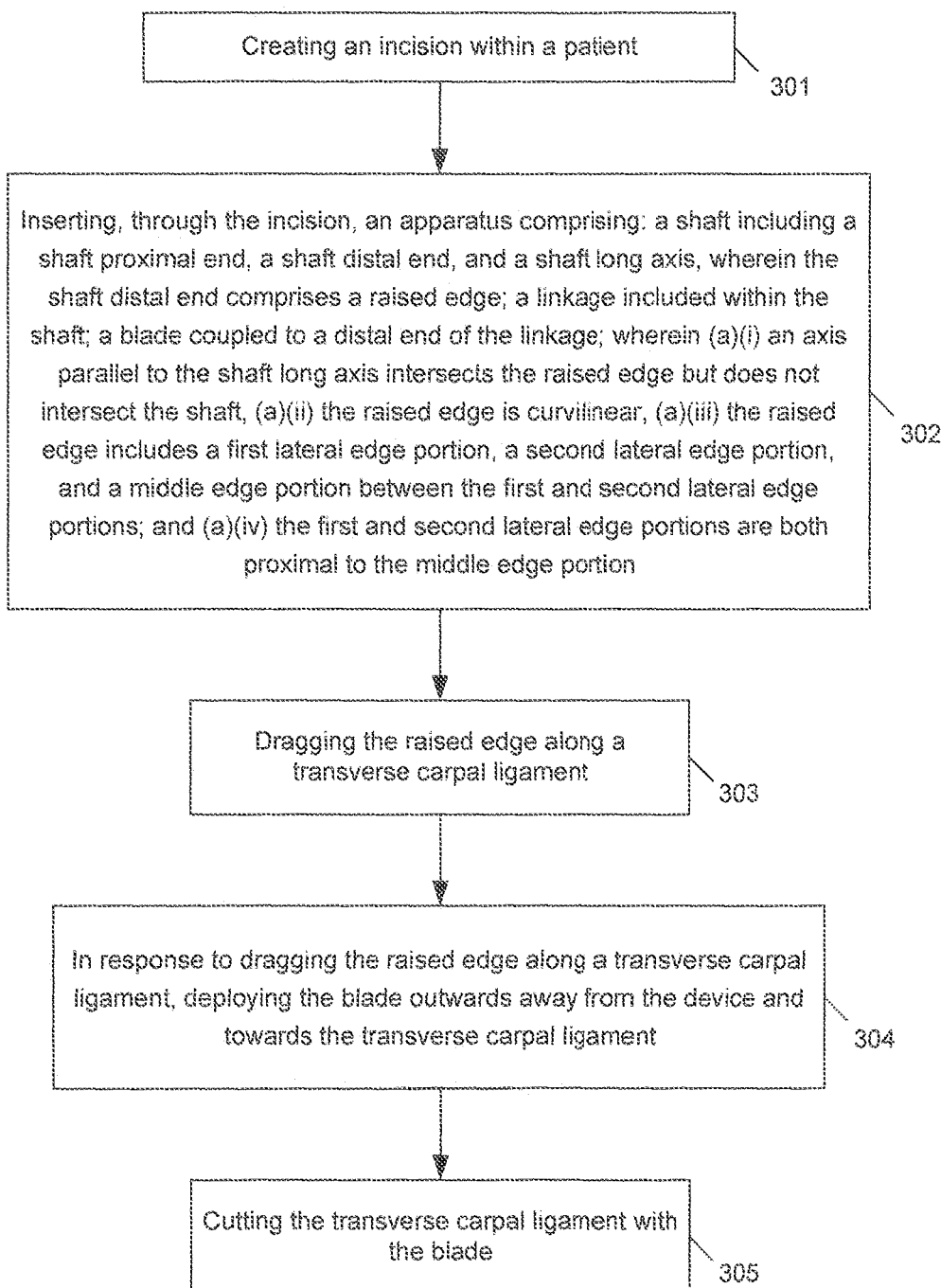

CARPAL TUNNEL RELEASE SYSTEMS AND METHODS

CROSS-REFERENCE TO RELATED APPLICATION

This application is a continuation of U.S. patent application Ser. No. 16/703,282, filed Dec. 4, 2019, which is a continuation of U.S. patent application Ser. No. 15/440,808, filed Feb. 23, 2017, now U.S. Pat. No. 10,499,942, issued Dec. 10, 2019, which claims priority to U.S. Provisional Patent Application No. 62/299,176 filed on Feb. 24, 2016 and entitled "Carpal Tunnel Release Systems and Methods." The content of each of the above applications is hereby incorporated by reference.

BACKGROUND

Carpal tunnel syndrome is caused by pressure on the median nerve within the carpal tunnel at the wrist. The carpal tunnel is composed of wrist bones on the back or dorsal side and the thick transverse carpal ligament volar. In between the wrist bones and the ligament are the flexor tendons and the median nerve.

Carpal tunnel syndrome symptoms include numbness and tingling in the thumb, index, middle and half of the ring digit. Other symptoms can include dropping things and pain. Treatment for carpal tunnel syndrome includes a procedure to release the transverse carpal ligament.

There are two conventional ways to perform this procedure: open and endoscopic. In the open procedure the surgeon uses a blade to cut down through the skin to cut the transverse carpal ligament. In the endoscopic procedure the surgeon makes one or two smaller incisions and inserts a device with a camera and a deployable blade to cut the transverse carpal from the underside. The endoscopic procedure avoids an incision in the palm and leads to quicker healing times as compared to the open method. These two procedures are typically preformed in an operating room with the patient sedated or asleep and with a tourniquet on the arm (to stop the blood flow to the arm) so the surgeon can see either with direct vision or with the camera.

BRIEF DESCRIPTION OF THE DRAWINGS

Features and advantages of embodiments of the present invention will become apparent from the appended claims, the following detailed description of one or more example embodiments, and the corresponding figures. Where considered appropriate, reference labels have been repeated among the figures to indicate corresponding or analogous elements.

FIG. 3 includes a method in an embodiment.

DETAILED DESCRIPTION

Figure 1A:
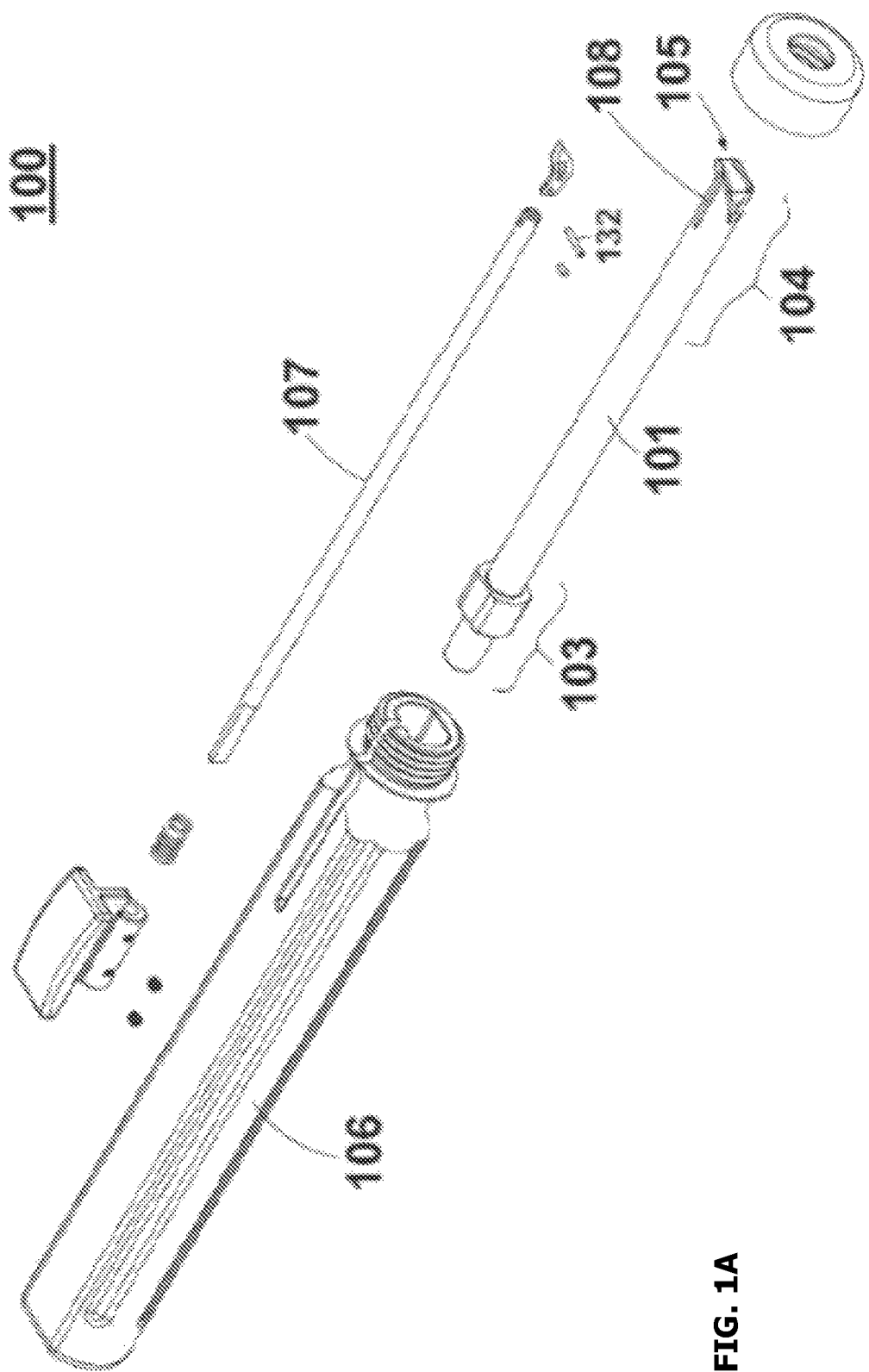
FIG. 1A includes an assembly drawing of an embodiment.

Reference will now be made to the drawings wherein like structures may be provided with like suffix reference designations. In order to show the structures of various embodiments more clearly, the drawings included herein are diagrammatic representations of structures. Moreover, the drawings may only show the structures useful to understand the illustrated embodiments. Additional structures known in the art may not have been included to maintain the clarity of the drawings. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner. "Connected" may indicate elements are in direct physical or electrical contact with each other and "coupled" may indicate elements co-operate or interact with each other, but they may or may not be in direct physical or electrical contact.

An embodiment includes a surgical device to perform carpal tunnel release. Such an embodiment allows the surgeon to move a procedure from the operating room to the office setting as there is no need for general anesthesia. Further, the embodiment saves money and time. The embodiment gives tactile feedback to the surgeon so the procedure can be done without a camera (e.g., endoscope), without a tourniquet (which is more comfortable for the patient), and under local anesthesia. An embodiment employs a 1 cm transverse incision made at the wrist crease. The instrument is inserted through the incision and the physician is able to feel the undersurface of the transverse carpal ligament indirectly via an edge of the instrument. A blade is then deployed via the instrument and by the surgeon and the ligament is cut.

In an embodiment a surgical instrument is used for blunt tissue dissection and for carpal tunnel release. The distal tip of the instrument projects upward (e.g., curved upward) so as to give a specific tactile feel when the surgeon is using the instrument to bluntly dissect soft tissue from the under surface of the transverse carpal ligament. The top of the distal tip of the instrument has a flat surface in the center that slopes down on both sides to a rounded bottom. The flat surface keeps the area on the transverse carpal ligament clear from soft tissue so that the deployable blade will not injure any soft tissue and will be able to transect the transverse carpal ligament safely.

An embodiment includes a unit (e.g., a single unit) composed of a proximal ergonomic handle with a mechanism (e.g., linkage coupled to a resilient member) to deploy a surgical blade that is located at the distal end of the device. The blade will be deployed by the operator's same hand that is holding the device through depression or advancement of a mechanism (e.g., a button or projection coupled to the linkage). The device is 12-20 cm in length. The shaft of the device has a flat top surface approximately 1-3 mm in width.

The top surface tapers at a 30 to 45 degree angle on each side to a rounded bottom the lower surface. The shaft is cylindrical in shape and the inside area of the device houses the surgical blade and the mechanism for deployment of the blade. The distal 5-10 mm of the shaft has 30-45 degree angle (with reference to a long axis of the shaft) of the distal tip. The surgical blade is deployed from the distal tip.

In an embodiment the distal tip of the surgical device has a distal edge that tapers down to 0.01-1 mm in thickness and in the shape of a semi-circle. This edge when engaged with the undersurface of the transverse carpal ligament in a proximal to distal motion will give a unique washboard feel.

In an embodiment the distal angle of the shaft and the distal edge of the device allow for the tactile feedback to allow this procedure to be done safely and effectively without visualization.

Various embodiments have different shapes compared to conventional systems. For example, an embodiment has a sharp distal edge that gives a specific feel when in contact with the transverse carpal ligament. This provides an advantage because surgical decisions can be made based on feel or tactile feedback. This allows the procedure to be performed without an endoscope, without a tourniquet (because sight, which would be obscured by blood but for the tourniquet), and using a smaller incision (no need for scope).

FIGS. 1A-1D and 2A-2E address embodiments that are now addressed.

An apparatus 100 comprises a shaft 101 including a shaft proximal end 103, a shaft distal end 104, and a shaft long axis 102. The shaft distal end comprises a raised edge 105. Handle 106 is coupled to the shaft proximal end 103. Linkage 107 is included within the shaft 101. Aperture 108 is included within a sidewall 109 of the shaft and also within a sidewall 110 of the raised edge 105. A blade 111 is coupled to a distal end of the linkage 107. The blade is configured to project outwards 112, away from the shaft long axis 102, when projected distally by the linkage 107. An axis 102' parallel to the shaft long axis 102 intersects the raised edge but does not intersect the shaft (see FIG. 2E).

Figure 2A:
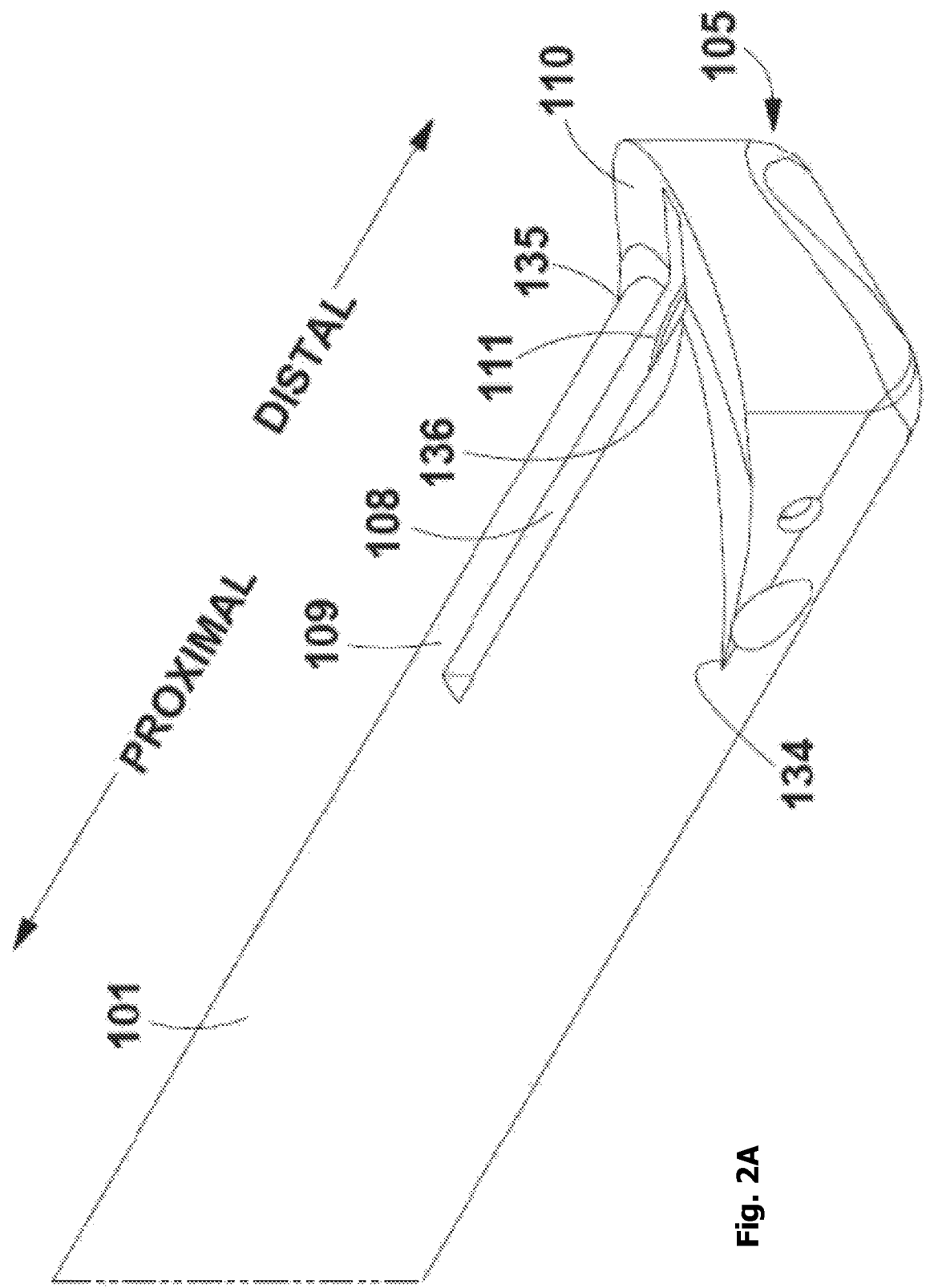
FIG. 2A includes a perspective view of a distal end portion of an embodiment with a blade not yet deployed.
Figure 2B:
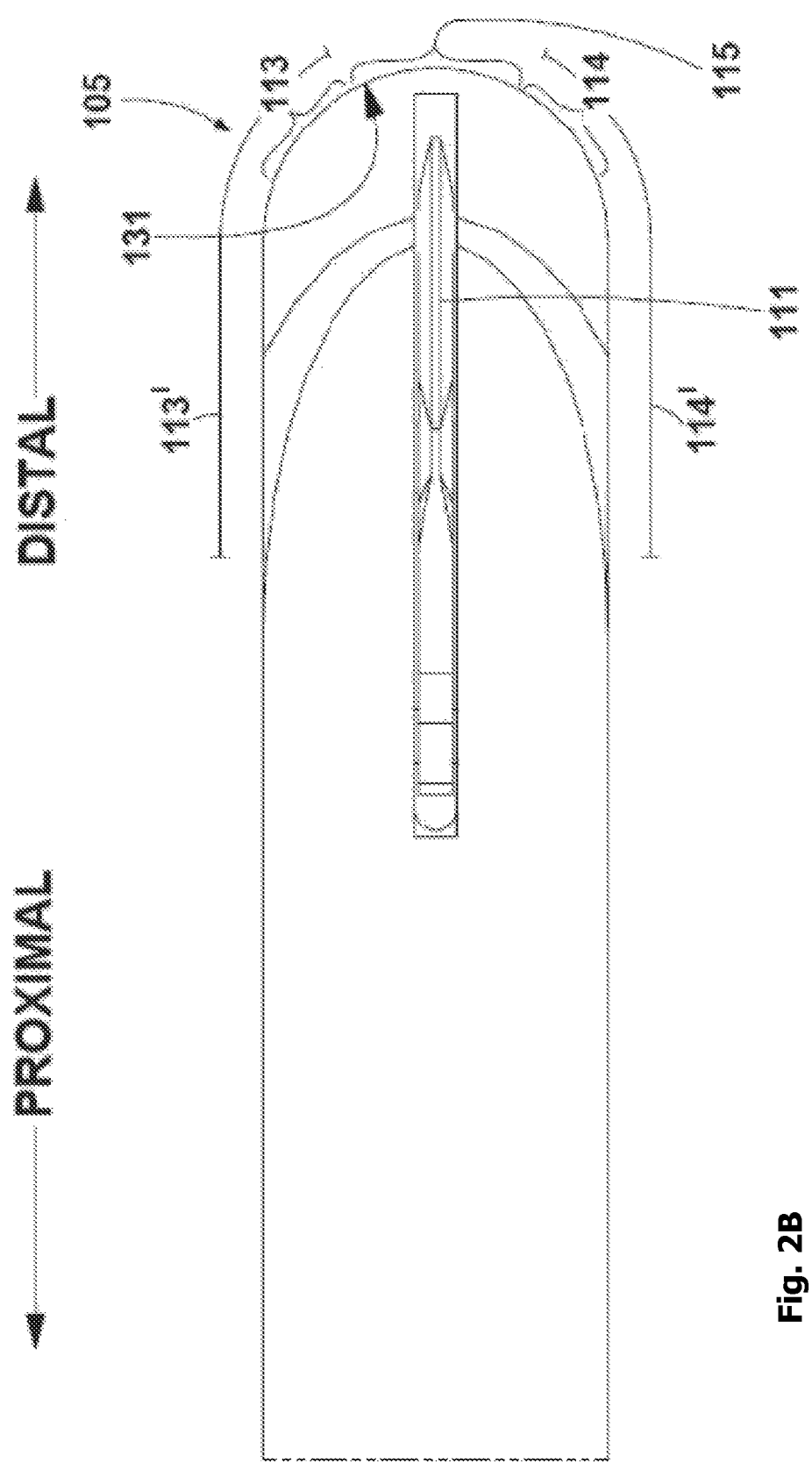
FIG. 2B includes a top view of the distal end portion of the embodiment with the blade not yet deployed.
Figure 2C:
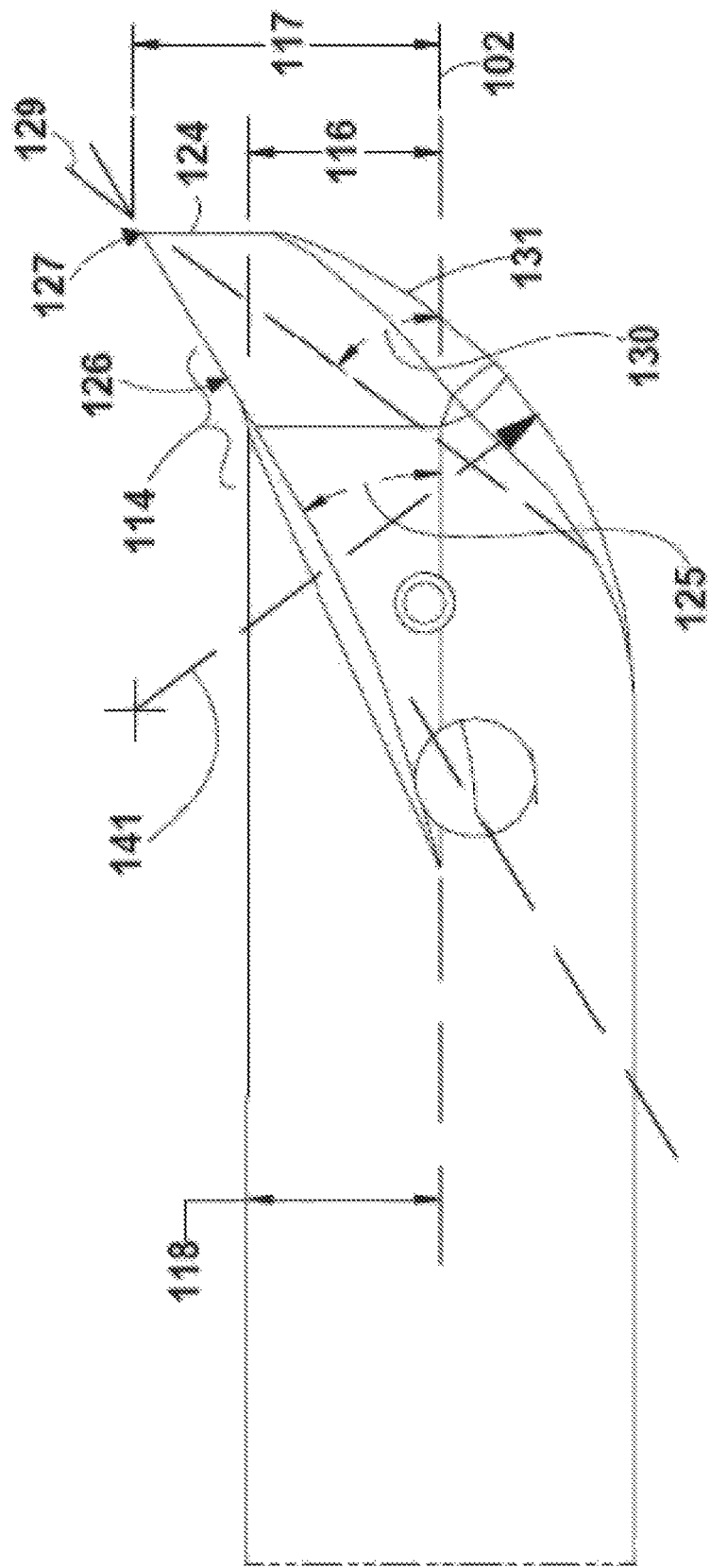
FIG. 2C includes a side view of the distal end portion of the embodiment with the blade not yet deployed.
Figure 2D:
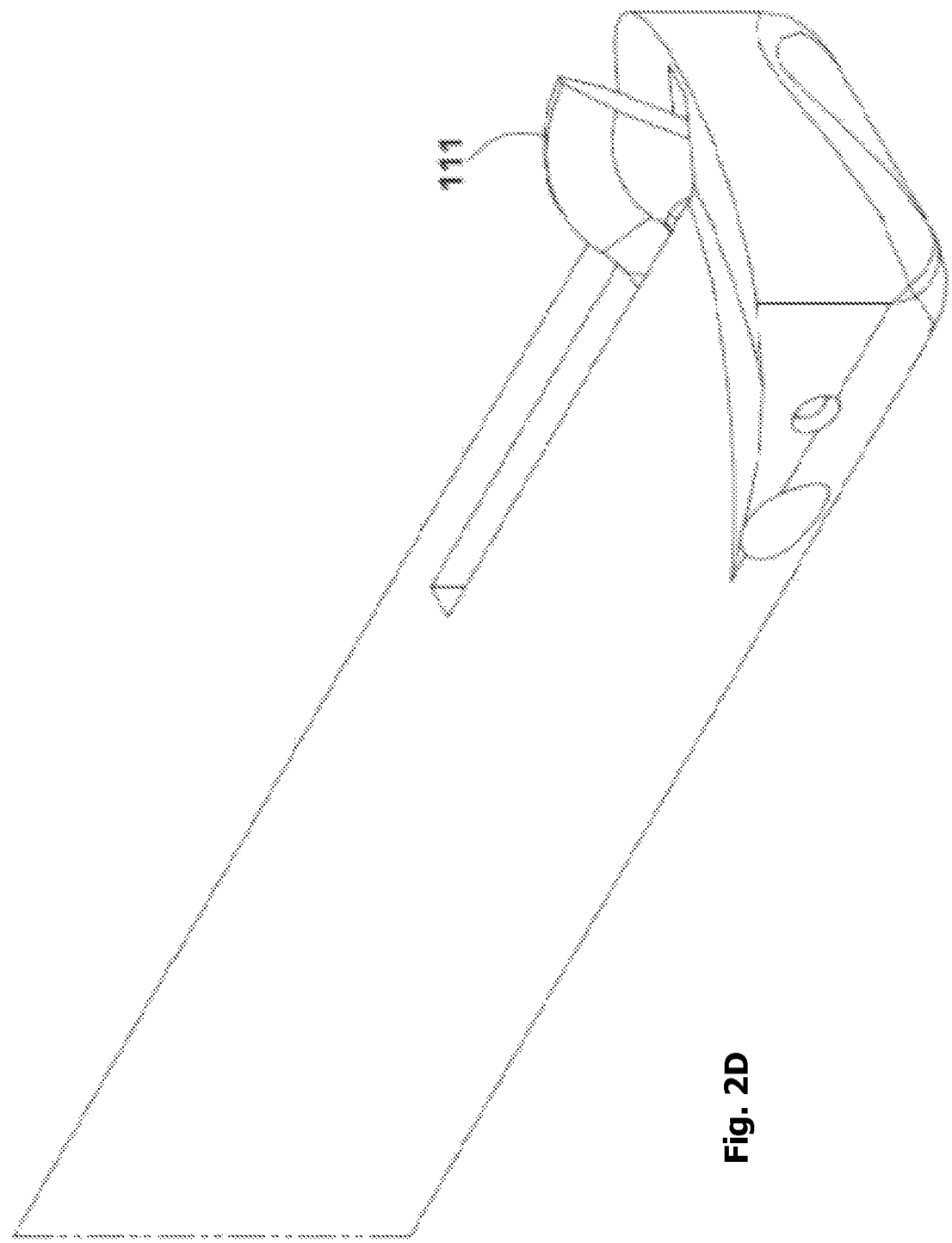
FIG. 2D includes a perspective view of the distal end portion of the embodiment with the blade deployed.

Raised edge 105 includes a sharpened point 127 (FIG. 2C). The point is not sharpened to the extent that it will cut tissue (blade 111 will be used to cut tissue) but is sharp enough to help provide tactile feedback when scraped along an undersurface of the ribbed transverse carpal ligament in a proximal to distal motion (or vice versa) will give a unique washboard feel.

While aperture 108 is shown to be narrow in FIG. 2A in other embodiments the aperture may be much wider and may generally include the majority of the volume of raised edge 105 and/or portions of distal end 104.

In FIG. 2B the raised edge includes a first lateral edge portion 113 (which is part of larger lateral edge 113'), a second lateral edge portion 114 (which is part of larger lateral edge 114'), and a middle edge portion 115 between the first and second lateral edge portions. The first and second lateral edge portions 113, 114 are both proximal to the middle edge portion. The raised edge is curvilinear. For example, portions 113, 114, 115 form a curved line visible in the plane shown in FIG. 2B (see surface 131). This curvilinear feature helps gently push tissue away when advancing the raised edge 105 distally within a patient's wrist.

Figure 2E:
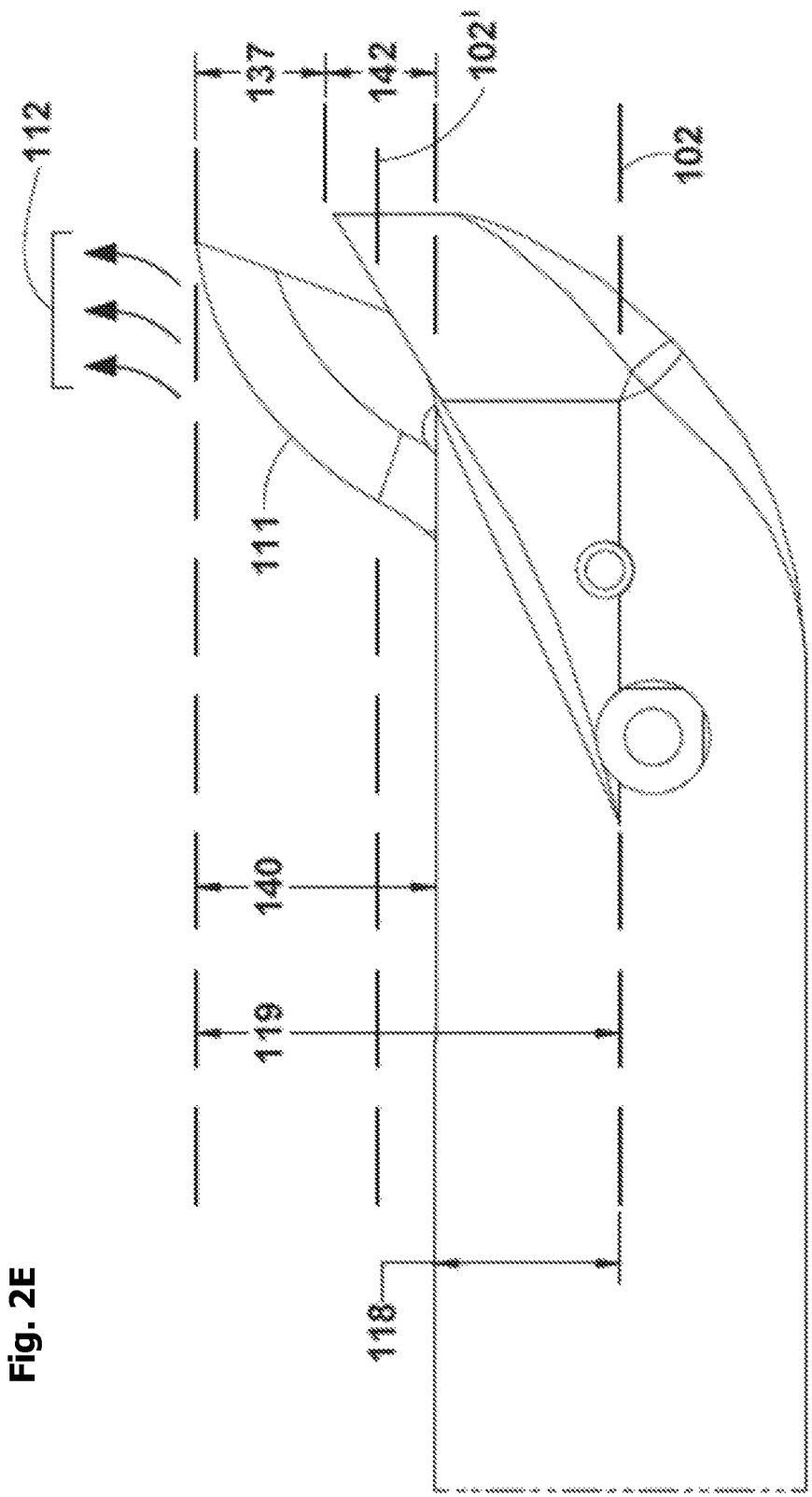
FIG. 2E includes a side view of the distal end portion of the embodiment with the blade deployed.

In FIG. 2C the first lateral edge portion extends a first radial distance 116 from the shaft long axis 102; the second lateral edge portion extends a second radial distance (not shown but equal to 116) from the shaft long axis; the middle edge portion extends a third radial distance 117 from the shaft long axis. The first and third radial distances are orthogonal to the shaft long axis 102. The third radial distance 117 is greater than first radial distance 116. In addition, an outer surface of a sidewall of the shaft is a fourth radial distance 118 from the shaft long axis 102. As seen in FIG. 2E, the blade 111, when fully deployed, extends a fifth radial distance 119 from the shaft long axis. The fourth and fifth radial distances are orthogonal to the shaft long axis 102. The third radial distance 117 is greater than the fourth radial distance 118 and less than the fifth radial distance 119.

The raised edge (distance 117) allows the surgeon to feel the ribbed undersurface of the transverse carpal ligament. The ability for the blade to rise above distance 117 (distance 119) allows the surgeon to deploy the blade only when determined safe to do so. The exposed blade (FIG. 2E) has sufficient clearance 137 to make meaningful deep incisions within the transverse carpal ligament, which allows the procedure to be completely quickly.

Figure 1C:
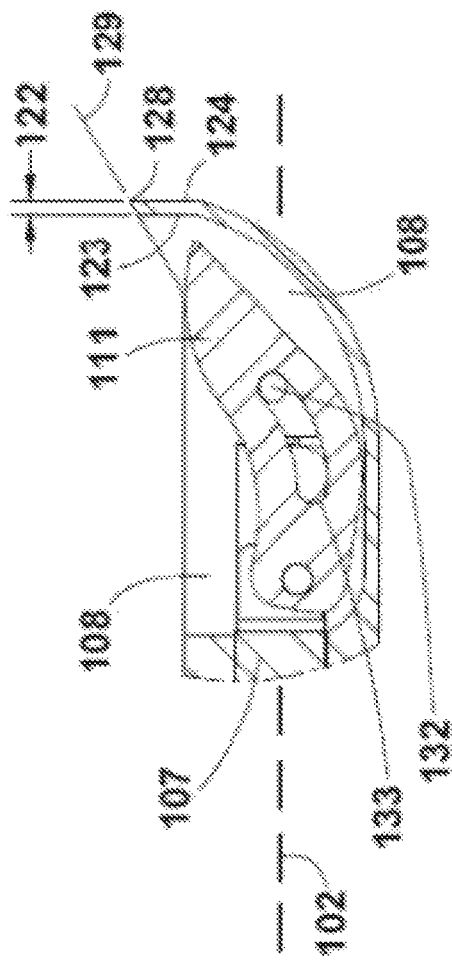
FIG. 1C includes a cross-section includes a cross-section view of a distal end portion of the embodiment.
Figure 1B:
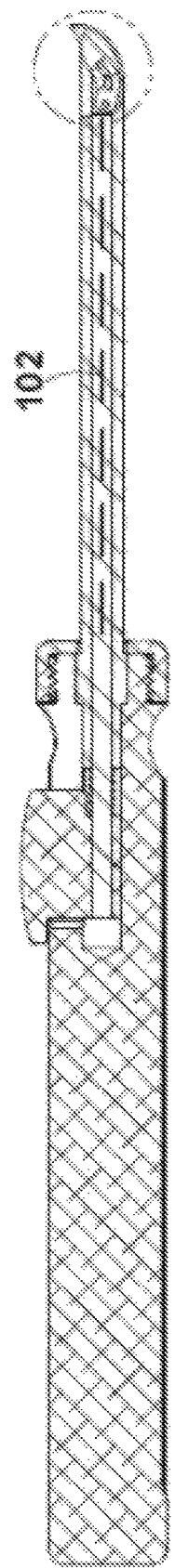
FIG. 1B includes a cross-section view of the embodiment.
Figure 1D:
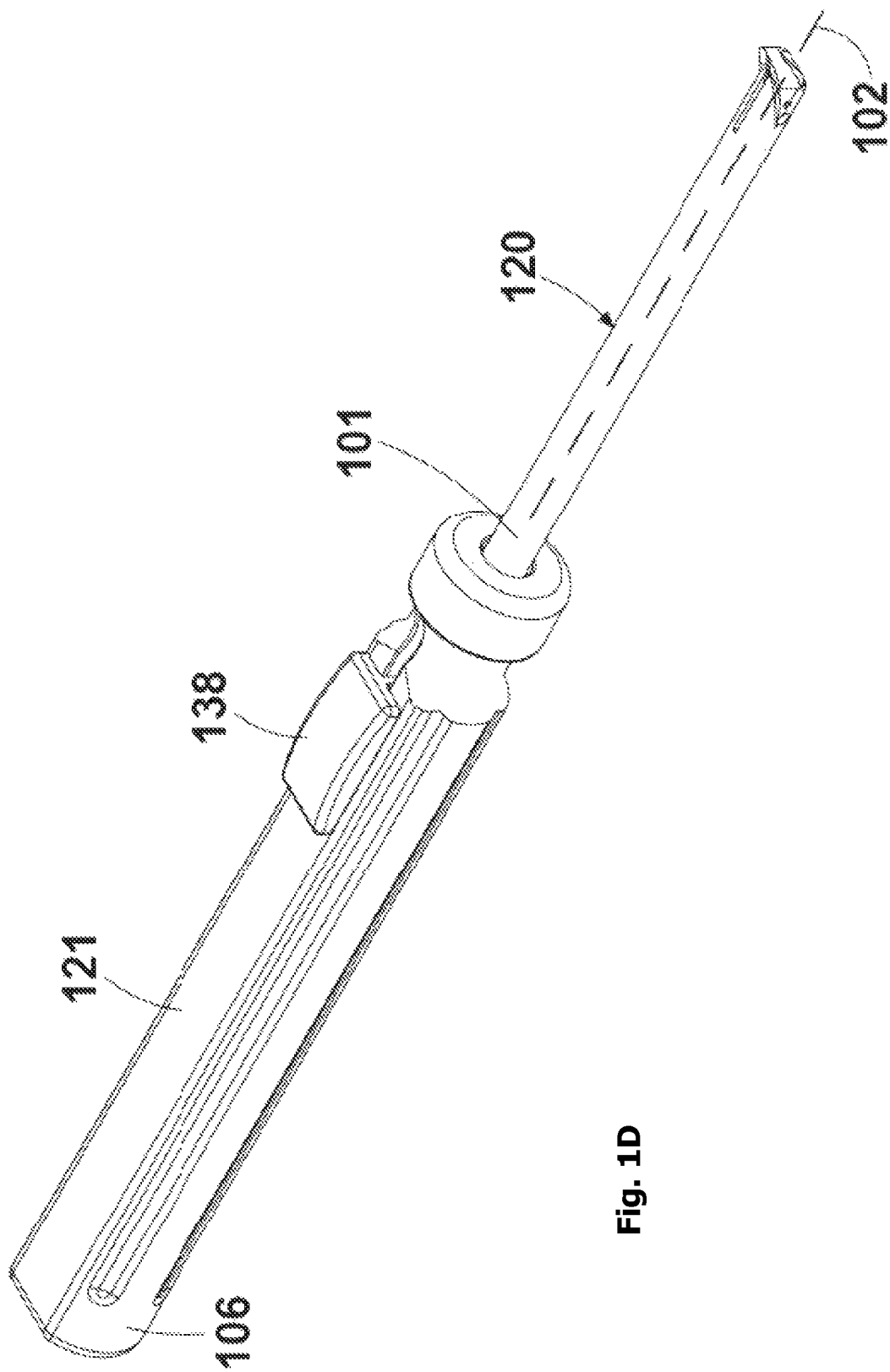
FIG. 1D includes a perspective view of the embodiment.

In the embodiment of FIG. 1D the sidewall of the shaft includes a portion, which is orthogonal to the shaft long axis 102, which is curvilinear. For example, shaft 101 includes a curved surface because shaft 101 may be a cylinder with a circular or ovular cross-section. In contrast, handle 106 may include a non-curvilinear surface 121. The curved "top" surface of the shaft allows for gradual displace of tissue when the surgeon pulls "up" on the device to engage the raised edge 105 with the transverse carpal ligament to gain tactile feedback indicative of properly engagement with the ligament. However, other embodiments may include a flattened "top surface" (or triangular surface and the like) on the same side of the device as the raised edge.

In the embodiment of FIG. 1C, the raised edge includes a thickness 122 between two sidewalls 123, 124 of the raised edge. The thickness 122, which is measured parallel to the shaft long axis 102, is less than 0.03 inches. Further, the aperture 108 directly interfaces one of the sidewalls (sidewall 123) of the raised edge. The narrow thickness 122 allows for a concentrated "sharp" feedback to the surgeon regarding the ribbed surface of the transverse carpal ligament, whereas a thicker wall that is not pointed (see point 127) would only provide dull feedback making proper identification of engagement with the transverse carpal ligament more difficult.

In the embodiment of FIG. 2C the raised edge includes lateral edge portion 114 with top exposed surface 126 that projects at an angle 125 with respect to the shaft long axis 102. Angle 125 is greater than 20 degrees. As shown in FIG. 2A, the aperture 108 is located in a top sidewall of the shaft 101 (to define "top" as used herein). In an embodiment, angle 125 is more than 20 degrees and less than 40 degrees.

The angle allows for a concentrated "sharp" feedback to the surgeon regarding the ribbed surface of the transverse carpal ligament, whereas a shallower angle would only provide dull feedback making proper identification of engagement with the transverse carpal ligament more difficult.

In the embodiment of FIG. 2C the raised edge includes a pointed tip 127 formed by two sidewall portions 124, 128 (see FIG. 1C). An additional axis 129 traverses the pointed tip and bisects a distance between the two sidewall portions; the additional axis projects at an additional angle 130 with respect to the shaft long axis. The additional angle 130 is greater than 20 degrees. In an embodiment, the angle 130 is greater than angle 125.

Again, the acuity of the angle 130 allows for a concentrated "sharp" feedback to the surgeon regarding the ribbed surface of the transverse carpal ligament, whereas a more obtuse angle would only provide dull feedback making proper identification of engagement with the transverse carpal ligament more difficult.

In the embodiment of FIG. 2B the shaft distal end includes an arcuate surface 131 that is curvilinear in a first plane. For example, FIG. 2B shows a horizontal plane. The embodiment of FIG. 2C shows how the surface 131 is also an arcuate surface that is curvilinear in a second plane. For example, FIG. 2C shows a vertical plane. This curvilinear surface is determined by radius of curvature 141. This arcuate surface helps gently push tissue away when advancing the raised edge 105 distally within a patient's wrist.

In the embodiment of FIG. 1C device 100 includes a dowel pin 132 traversing an additional aperture 133 included in the blade 111. The pin 132/aperture 133 orientation allows the blade to project "upwards" (direction 112) when the linkage 107 advances distally due to the surgeon manipulating projection 138 distally.

In the embodiment of FIG. 2A proximal-most locations 134, 135 of the first and second lateral edge portions contact the shaft 101 proximal to where a proximal-most location 136 of the middle edge portion contacts the shaft. Such an arrangement is not required in all embodiments but may help facilitate creation of arcuate surfaces (e.g., surface 131) and coupling such surfaces to an arcuate upper surface of shaft 101.

FIG. 3 includes a method 300 in an embodiment. Block 301 includes creating an incision within a patient. In an embodiment no tourniquet is used during method 300. In an embodiment general anesthesia is not used during method 300 but instead the incision of block 301 and method 300 are performed under local anesthesia.

Block 302 includes inserting, through the incision, an apparatus comprising: a shaft including a shaft proximal end, a shaft distal end, and a shaft long axis, wherein the shaft distal end comprises a raised edge; a linkage included within the shaft; a blade coupled to a distal end of the linkage; wherein (a)(i) an axis parallel to the shaft long axis intersects the raised edge but does not intersect the shaft, (a)(ii) the raised edge is curvilinear, (a)(iii) the raised edge includes a first lateral edge portion, a second lateral edge portion, and a middle edge portion between the first and second lateral edge portions; and (a)(iv) the first and second lateral edge portions are both proximal to the middle edge portion;

Block 303 includes dragging the raised edge along a transverse carpal ligament. In an embodiment block 303 occurs without using a camera (e.g., endoscope).

Block 304 includes, in response to dragging the raised edge along a transverse carpal ligament, deploying the blade outwards away from the device and towards the transverse carpal ligament. For example, in response to receiving feedback such as the sensation of the raised edge dragging across the ribbed ligament, the surgeon may consequently verify he or she is correctly positioned and that it is safe to deploy the blade.

Block 305 includes cutting the transverse carpal ligament with the blade.

Various ranges of dimensions are included in various embodiments. For example, in Embodiment A dimension 137 may be about 0.07 to 0.08 inches but in other embodiments may be 0.05-0.10 inches or more. In Embodiment A dimension 140 may be about 0.12 to 0.13 inches but in other embodiments may be 0.10-0.15 inches or more. In Embodiment A dimension 122 may be about 0.015 to 0.017 inches but in other embodiments may be 0.01-0.02 inches or more. Dimension 122 may be a thickness generally for the sidewalls of the shaft 101. Dimension 141 includes a radius of curvature and may be in Embodiment A about 0.23 to 0.26 inches but in other embodiments may be 0.2-0.3 inches or more. Dimension 117 may be about 0.14 to 0.16 inches in Embodiment A but in other embodiments may be 0.1-0.2 inches or more. The length of shaft 101 (including raided edge 105) that emanates from handle 106 is about 3.0 to 3.2 inches in Embodiment A but may be longer or shorter in other embodiments. The width of shaft 101 (taken orthogonal to axis 102) is about 0.2 to 0.3 inches in Embodiment A but may be wider or narrower in other embodiments. The width of aperture 108 (taken orthogonal to axis 102) is about 0.02 to 0.03 inches in Embodiment A but may be wider or narrower in other embodiments. For example, in other embodiments the aperture may approximate the width of the shaft. For example, dimension 142 may be about 0.05 to 0.06 inches in Embodiment A but in other embodiments may be 0.04-0.08 inches or more.

Some dimension may be critical. For example, in an embodiment it is critical that dimension 142 be tall enough, and that tip 127 be acute enough, and that angle 125 be large enough to provide tactile feedback to the surgeon when dragging the raised edge across the ribbed surface of a target ligament, tendon, muscle, or other tissue.

In other embodiments other cutting means besides a blade may be used. For example, in other embodiments a cautery device may have a tip that deploys similar to how the aforementioned blade deploys (e.g., via a linkage and possibly a resilient member (e.g., spring) addressed in FIG. 1A).

Figure 4:
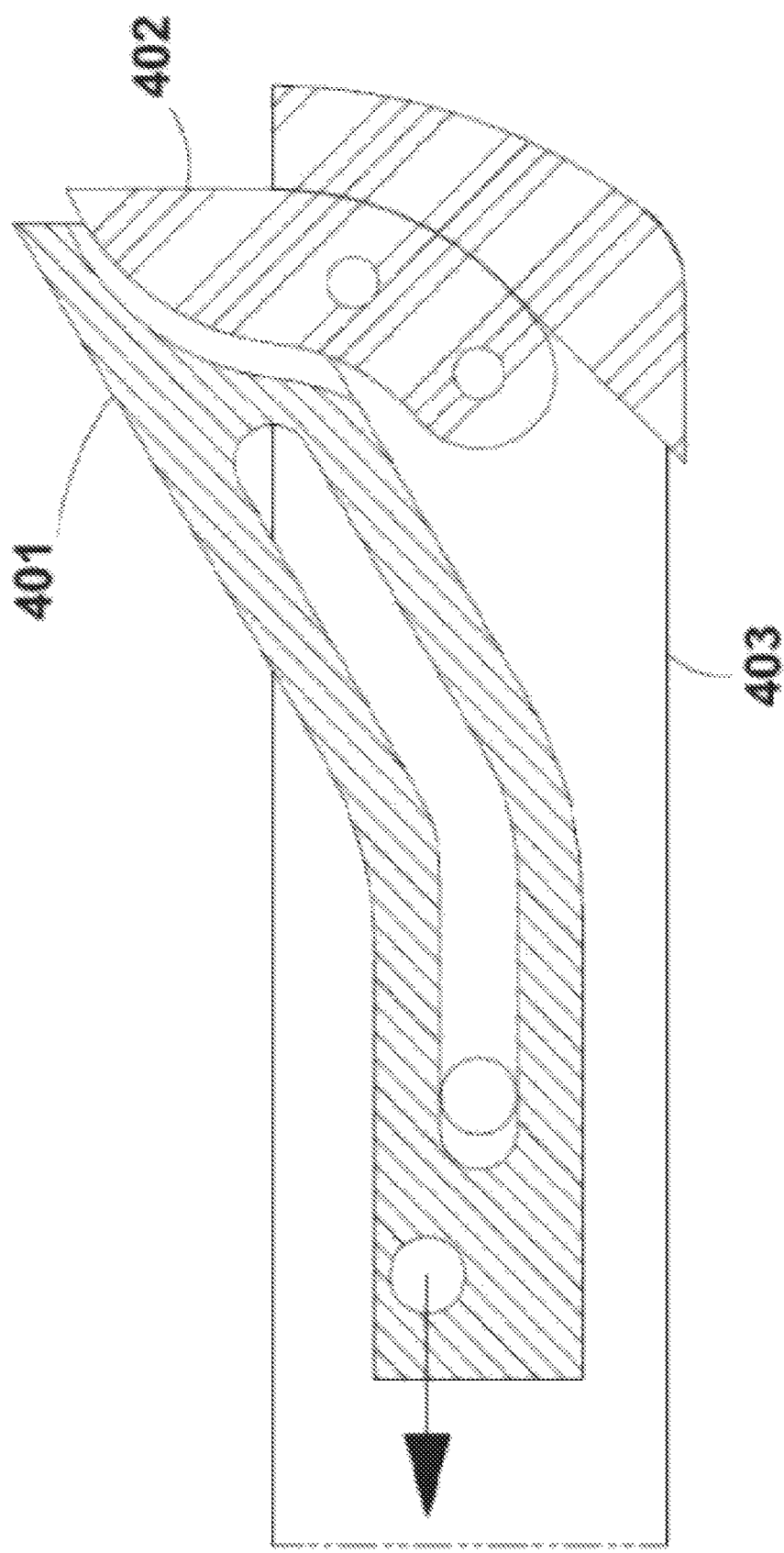
FIG. 4 includes an embodiment.

FIG. 4 includes an embodiment that includes a shield 401 for the blade 402. In such an embodiment the blade may be static and the shield may be dynamic. For example, a portion of the blade may statically be positioned over the shaft 403. Shield 401 may be coupled to a linkage and deployed over the blade 402. The shield may be withdrawn via the linkage when the surgeon is ready to incise tissue.

Figure 5:
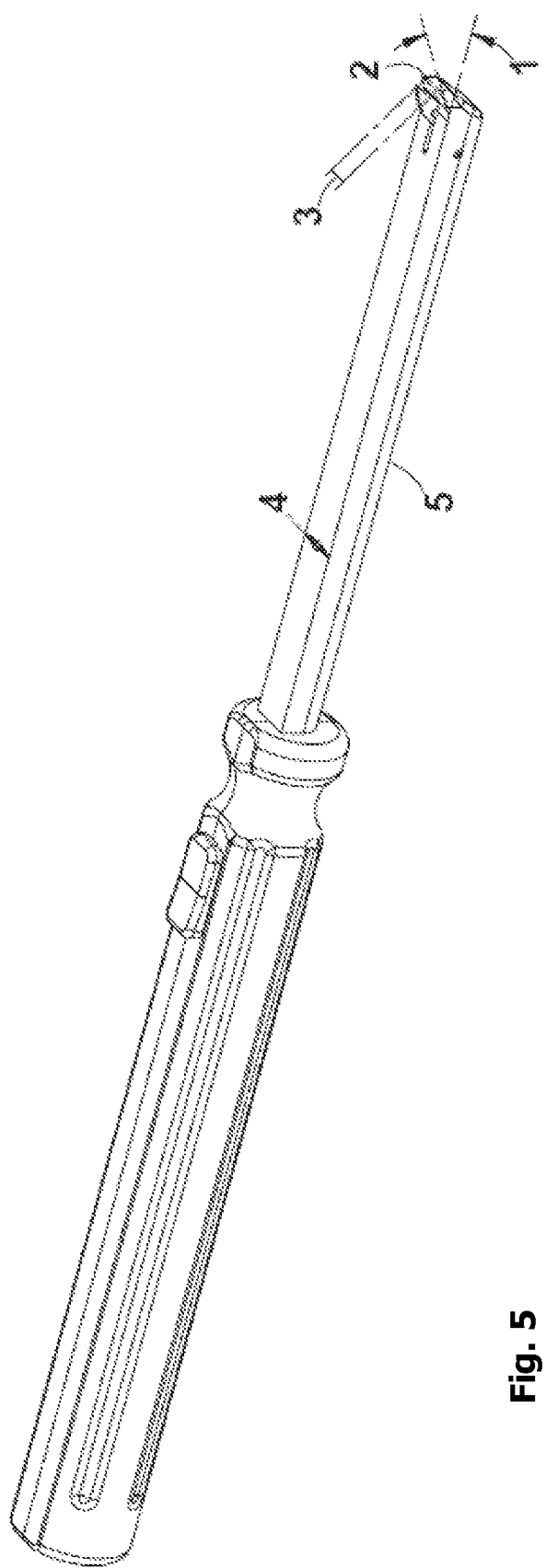
FIG. 5 includes an embodiment.

FIG. 5 includes an embodiment. Angle 1 allows for surface 2 to better engage tissue (because it ensures the surface 2 rises about the main shaft). The breadth/width 3 of surface 2 allows for the washboard sensation that is used in lieu of visualization. In other words, the wide breadth (relatively speaking) provides more surface area to move across the connective tissue and helps the surgeon register the washboard feel of a proper location to dissect the tissue.

There are at least two unique attributes to the embodiment of FIG. 5: First, the relatively sharply angled distal end (distal end projects away from linear main shaft)—see angle 1. Second, the most distal, most superior edge (see edge 2, with breadth 3) is linear with a relatively long surface (e.g., approaching or at width 4 of shaft 5) with which to better feel the connective tissue.

Figure 6:
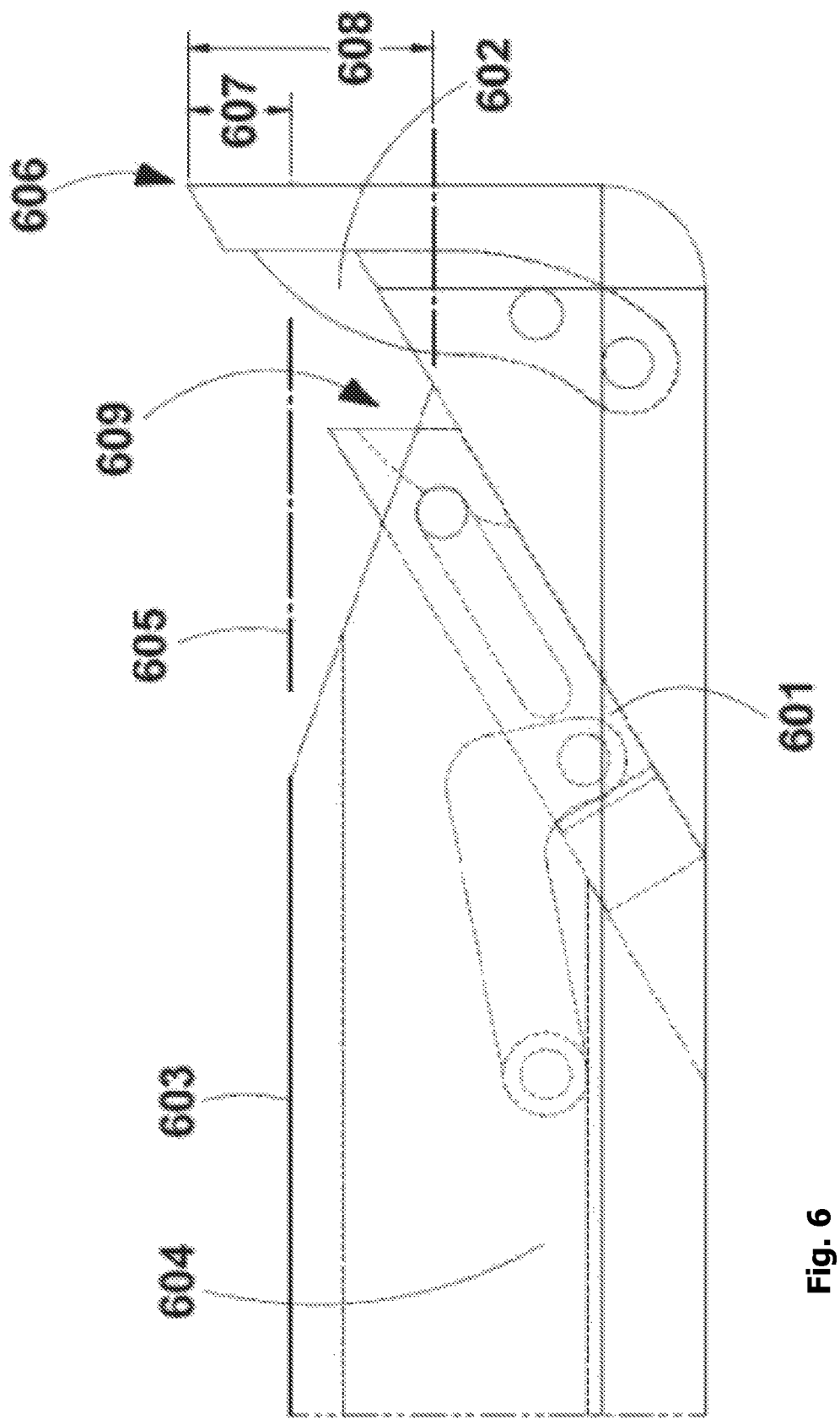
FIG. 6 includes an embodiment.

FIG. 6 includes an embodiment that includes a shield 601 for the blade 602. In such an embodiment the blade may be static and the shield may be dynamic. For example, a portion of the blade may statically be positioned over the shaft 603 (see how blade extends over line 605). Shield 601 may be coupled to a linkage 604 and deployed over the blade 602. The shield may be withdrawn via the linkage when the surgeon is ready to incise tissue.

FIG. 6 depicts an aspect that may be included in other embodiments. For example, distal edge 606 may extend a first amount 607 above the main shaft body 603 but a greater second amount 608 above a depression 609 in the shaft. In an embodiment blade 602 and/or tip 606 may not extend above line 605 but may still be effective because 606 still provides a tip to drag across target ligaments and is still "relatively elevated" above other surfaces due to depression 609 (i.e., tip 606 is elevated with regard to adjacent depression 609 even though tip 606 is not elevated with regard to more "distantly" located main shaft body 603). This may provide manufacturing advantages for the device. A surgeon may be able to cut the ligament with blade 602 by rotating the distal end of the device about a proximally located pivot point (e.g., the handle). Doing so may drive tissue into depression 609 where the tissue can be incised.

There are at least three unique attributes to various embodiments described herein. First, the angle (e.g., angle 125 of FIG. 2C) at which the distal portion of the shaft projects up from the shaft. Second, the angle of the most distal edge as it tapers down to that distal edge which engages the tissue (e.g., how height 116 is less than height 117 of FIG. 2C). Third, the shape of the most distal projection (e.g., in an embodiment the shape is bulbous having arcuate surfaces horizontal and/or vertical planes). These advantages allow for carpel tunnel release without visualization (and the need for a tourniquet that corresponds to visualization). The need for a more simplified procedure was identified by Applicant and embodiments addressed herein address Applicant's identified problem of how to more quickly and simply perform carpel tunnel release without visualization or a tourniquet.

Various examples follow.

Example 1 includes an apparatus comprising: a shaft including a shaft proximal end, a shaft distal end, and a shaft long axis, wherein the shaft distal end comprises a raised edge; a handle coupled to the shaft proximal end; a linkage included within the shaft; an aperture included within a sidewall of the shaft and also within a sidewall of the raised edge; and a blade coupled to a distal end of the linkage; wherein (a)(i) the blade is configured to project outwards, away from the shaft long axis, when projected distally by the linkage, (a)(ii) an axis parallel to the shaft long axis intersects the raised edge but does not intersect the shaft.

Example 2 includes the apparatus of example 1 wherein the raised edge is curvilinear.

Example 3 includes the apparatus of example 2 wherein: the raised edge includes a first lateral edge portion, a second lateral edge portion, and a middle edge portion between the first and second lateral edge portions; the first and second lateral edge portions are both proximal to the middle edge portion.

Example 4 includes the apparatus of example 3 wherein: the first lateral edge portion extends a first radial distance from the shaft long axis; the second lateral edge portion extends a second radial distance from the shaft long axis; the middle edge portion extends a third radial distance from the shaft long axis; the first, second, and third radial distances are orthogonal to the shaft long axis; the third radial distance is greater than both of the first and second radial distances.

Example 5 includes the apparatus of example 4 wherein: an outer surface of a sidewall of the shaft is a fourth radial distance from the shaft long axis; the blade, when fully deployed, extends a fifth radial distance from the shaft long axis; the fourth and fifth radial distances are orthogonal to the shaft long axis; and the third radial distance is greater than the fourth radial distance and less than the fifth radial distance.

Another version of example includes the apparatus of example 4 wherein: an outer surface of a sidewall of the shaft is a fourth radial distance from the shaft long axis; the blade, when fully deployed, extends a fifth radial distance from the shaft long axis; the fourth and fifth radial distances are orthogonal to the shaft long axis; and the third radial distance is the maximum distance any portion of the apparatus distal of the handle extends away from the shaft long axis; the third radial distance is greater than the fourth radial distance and less than the fifth radial distance.

If, for example, the blade does not extend higher than any portion of the device distal of the handle this will adversely affect the ability of the surgeon to closely fill the ribbed undersurface of the ligament and then deploy a blade in immediate proximity of the tip used for feedback. As such the surgeon does not have to maneuver the device into position once the desired ligament location has been determined.

Example 6 includes the apparatus of example 5 wherein the sidewall of the shaft includes a portion, which is orthogonal to the shaft long axis, which is curvilinear.

Example 7 includes the apparatus of example 5 wherein: the raised edge includes a thickness between two sidewalls of the raised edge; the thickness, which is parallel to the shaft long axis, is less than 0.03 inches; the aperture directly interfaces one of the sidewalls of the raised edge.

Example 8 includes the apparatus of example 7 wherein: at least one of the first and second lateral edge portions and the middle edge portion includes a top exposed surface that projects at an angle with respect to the shaft long axis; the angle is greater than 20 degrees; and the aperture is located in a top sidewall of the shaft.

Example 9 includes the apparatus of example 8 wherein: the angle is less than 40 degrees; the shaft includes a shaft middle portion between the shaft proximal end and the shaft distal end; the shaft middle portion and the shaft proximal end are non-curvilinear; the shaft includes an interior chamber that includes the linkage; the aperture includes a narrow slot configured to narrowly receive the blade and exclude tissue from entering into interior chamber.

Another version of example 9 includes the apparatus of example 8 wherein: the angle is less than 40 degrees; the shaft includes a shaft middle portion between the shaft proximal end and the shaft distal end; the shaft middle portion and the shaft proximal end are non-curvilinear; the shaft includes an interior chamber that includes the linkage; the aperture includes a narrow slot configured to narrowly receive the blade and exclude tissue from entering into interior chamber.

For example, a long sloping or curved shaft would not be conducive to practicing a method of the invention. Such a method includes placing the shaft with force upwards against the ligament and then moving the shaft back and forth in an attempt to feel the ribbed surface of the ligament with the raised surface. Having a generally linear shaft (which is generally linear from the handle to the raised edge)(which in some embodiments has curvilinear surface taken orthogonal to axis 102 to help dissect tissue immediately beneath the ligament) facilitates proximity of the device towards the area to sever. The surgeon may locate the shaft against the ligament and then pull upwards/superiorly. While doing so the surgeon may withdraw or move the device proximally until the raised edge detects the ribbed undersurface. While still pulling upwards the blade is deployed without repositioning the device. The ligament is then severed in one or more attempts.

Example 10 includes the apparatus of example 9 wherein: the raised edge includes a pointed tip formed by two sidewall portions; an additional axis traverses the pointed tip and bisects a distance between the two sidewall portions; the additional axis projects at an additional angle with respect to the shaft long axis; the additional angle is greater than 20 degrees.

Another version of example 10 includes the apparatus of example 9 wherein: the raised edge includes a pointed tip formed by two sidewall portions; the pointed tip is at least partially defined by the thickness between the two sidewalls of the raised edge; an additional axis traverses the pointed tip and bisects a distance between the two sidewall portions; the additional axis projects at an additional angle with respect to the shaft long axis; the additional angle is greater than the angle.

Thus, having angle 130 be greater than angle 125 helps promote tactile feedback by forming a sharper angle between the point 127 and the ribbed undersurface of the ligament.

Example 11 includes the apparatus of example 10 wherein the shaft distal end includes an arcuate surface that is curvilinear in a first plane.

Example 12 includes the apparatus of example 10 wherein the shaft distal end includes an arcuate surface that is curvilinear in first and second planes that are orthogonal to each other.

Example 13 includes the apparatus of example 2 wherein: the raised edge includes a first lateral edge portion, a second lateral edge portion, and a middle edge portion between the first and second lateral edge portions; an outer surface of a sidewall of the shaft is a first radial distance from the shaft long axis; the middle edge portion includes a location with a second radial distance from the shaft long axis; the blade, when fully deployed, extends a third radial distance from the shaft long axis; the first, second, and third radial distances are orthogonal to the shaft long axis; the second radial distance is greater than the first radial distance and less than the third radial distance.

Example 14 includes the apparatus of example 2 comprising a dowel pin traversing an additional aperture included in the blade.

Example 15 includes the apparatus of example 2 wherein: the raised edge includes a first lateral edge portion, a second lateral edge portion, and a middle edge portion between the first and second lateral edge portions; and proximal-most locations of the first and second later edge portions contact the shaft proximal to where a proximal-most location of the middle edge portion contacts the shaft.

Example 16 includes an apparatus comprising: a shaft including a shaft proximal end, a shaft distal end, and a shaft long axis, wherein the shaft distal end comprises a raised edge; a linkage included within the shaft; a blade coupled to a distal end of the linkage; wherein (a)(i) an axis parallel to the shaft long axis intersects the raised edge but does not intersect the shaft, (a)(ii) the raised edge is curvilinear, (a)(iii) the raised edge includes a first lateral edge portion, a second lateral edge portion, and a middle edge portion between the first and second lateral edge portions; and (a)(iv) the first and second lateral edge portions are both proximal to the middle edge portion.

Example 17 includes the apparatus of example 16 wherein: the first lateral edge portion extends a first radial distance from the shaft long axis; the second lateral edge portion extends a second radial distance from the shaft long axis; the middle edge portion extends a third radial distance from the shaft long axis; an outer surface of a sidewall of the shaft is a fourth radial distance from the shaft long axis; the blade, when fully deployed, extends a fifth radial distance from the shaft long axis; the first, second, third, fourth and fifth radial distances are orthogonal to the shaft long axis; and the third radial distance is greater than first, second, and fourth radial distances and is less than the fifth radial distance.

Example 18 includes the apparatus of example 17 wherein: the raised edge includes a thickness, between two sidewalls of the raised edge, less than 0.03 inches; and at least one of the first and second lateral edge portions and the middle edge portion includes a top exposed surface that projects at an angle that is greater than 20 degrees with respect to the shaft long axis.

Example 19 includes the apparatus of example 18 wherein: the raised edge includes a pointed tip formed by two sidewall portions; an additional axis traverses the pointed tip and bisects a distance between the two sidewall portions; the additional axis projects at an additional angle with respect to the shaft long axis; and the additional angle is greater than 20 degrees.

Example 20 includes a method comprising: creating an incision within a patient; inserting, through the incision, an apparatus comprising: a shaft including a shaft proximal end, a shaft distal end, and a shaft long axis, wherein the shaft distal end comprises a raised edge; a linkage included within the shaft; a blade coupled to a distal end of the linkage; wherein (a)(i) an axis parallel to the shaft long axis intersects the raised edge but does not intersect the shaft, (a)(ii) the raised edge is curvilinear, (a)(iii) the raised edge includes a first lateral edge portion, a second lateral edge portion, and a middle edge portion between the first and second lateral edge portions; and (a)(iv) the first and second lateral edge portions are both proximal to the middle edge portion; dragging the raised edge along a transverse carpal ligament; in response to dragging the raised edge along a transverse carpal ligament, deploying the blade outwards away from the device and towards the transverse carpal ligament; and cutting the transverse carpal ligament with the blade.

The foregoing description of the embodiments of the invention has been presented for the purposes of illustration and description. It is not intended to be exhaustive or to limit the invention to the precise forms disclosed. This description may include terms, such as left, right, top, bottom, over, under, upper, lower, first, second, etc. that are used for descriptive purposes only and are not to be construed as limiting. The embodiments of a device described herein can be manufactured, used, or shipped in a number of positions and orientations. Persons skilled in the relevant art can appreciate that many modifications and variations are possible in light of the above teaching. Persons skilled in the art will recognize various equivalent combinations and substitutions for various components shown in the Figures. It is therefore intended that the scope of the invention be limited not by this detailed description.

What is claimed is:

1. An apparatus comprising:
   a first shaft including a first shaft proximal end, a first shaft distal end, and a first shaft long axis extending through the first shaft proximal and distal ends, wherein the first shaft distal end comprises a raised edge that extends away from the first shaft long axis;
   a handle coupled to the first shaft proximal end;
   a second shaft included within the first shaft;
   an aperture included within a sidewall of the first shaft; and
   a blade coupled to the second shaft;
   wherein (a)(i) the blade is configured to project outwards, away from the first shaft long axis, when at least a portion of the blade is moved distally by the second shaft, and (a)(ii) the first shaft distal end includes an arcuate surface that is curvilinear in first and second planes that are orthogonal to each other;

wherein (b)(i) the raised edge includes proximal and distal walls, (b)(ii) the proximal wall of the raised edge is distal to the handle and proximal to the distal wall of the raised edge, and (b)(iii) the proximal wall of the raised edge is configured to contact tissue when the raised edge contacts the tissue and the handle is moved proximally.

2. The apparatus of claim 1 wherein:
the raised edge includes a first lateral edge portion, a second lateral edge portion, and a middle edge portion coupling the first and second lateral edge portions to each other; and
the first and second lateral edge portions are both proximal to the middle edge portion.

3. The apparatus of claim 2 wherein:
at least one of the first lateral edge portion, the second lateral edge portion, or the middle edge portion includes a top exposed surface that projects at an acute angle with respect to the first shaft long axis;
the acute angle is greater than 20 degrees; and
the acute angle and an obtuse angle are supplementary angles with one another; and
the obtuse angle is proximal to the acute angle.

4. The apparatus of claim 3 wherein:
the acute angle is less than 40 degrees; and
the first shaft includes an interior chamber that includes the second shaft; and
the aperture includes a narrow slot configured to narrowly receive the blade and exclude tissue from entering into the interior chamber.

5. The apparatus of claim 3 wherein:
the raised edge includes a pointed tip formed by the proximal and distal walls of the raised edge;
the pointed tip is at least partially defined by a junction between the proximal and distal walls of the raised edge;
an additional axis traverses the pointed tip and bisects a distance between the proximal and distal walls of the raised edge;
the additional axis projects at an additional acute angle with respect to the first shaft long axis;
the additional acute angle is greater than the acute angle;
the additional acute angle and an additional obtuse angle are supplementary angles with one another; and
the additional obtuse angle is proximal to the additional acute angle.

6. E apparatus of claim 2 wherein:
the first lateral edge portion extends a first radial distance from the first shaft long axis, the first radial distance being a maximum distance the first lateral edge portion extends from the first shaft long axis;
the second lateral edge portion extends a second radial distance from the first shaft long axis, the second radial distance being a maximum distance the second lateral edge portion extends from the first shaft long axis;
the middle edge portion extends a third radial distance from the first shaft long axis, the third radial distance being a maximum distance the middle edge portion extends from the first shaft long axis;
the first, second, and third radial distances are orthogonal to the first shaft long axis; and
the third radial distance is greater than the first radial distance and the third radial distance is greater than the second radial distance.

7. The apparatus of claim 6 wherein:
an outer surface of the sidewall of the first shaft is a fourth radial distance from the first shaft long axis, the fourth radial distance being a maximum distance the outer surface of the sidewall of the first shaft extends from the first shaft long axis;
the blade, when fully deployed, extends a fifth radial distance from the first shaft long axis, the fifth radial distance being a maximum distance the fully deployed blade extends from the first shaft long axis;
the fourth and fifth radial distances are orthogonal to the first shaft long axis; and
the third radial distance is greater than the fourth radial distance and the third radial distance is less than the fifth radial distance.

8. The apparatus of claim 1 wherein:
the raised edge includes a maximum thickness between the proximal and distal walls of the raised edge;
the maximum thickness, which is parallel to the first shaft long axis, is less than 0.03 inches; and
the aperture directly interfaces at least one of the proximal or distal walls of the raised edge.

9. The apparatus of claim 1 wherein the raised edge is curvilinear.

10. The apparatus of claim 1, wherein:
the raised edge includes a maximum thickness between the proximal and distal walls of the raised edge;
the maximum thickness, which is parallel to the first shaft long axis, is less than 0.03 inches;
the aperture directly interfaces at least one of the proximal or distal walls of the raised edge; and
an axis parallel to the first shaft long axis intersects the raised edge but does not intersect the first shaft.

11. The apparatus of claim 1 wherein:
the raised edge includes a first lateral edge portion, a second lateral edge portion, and a middle edge portion between the first and second lateral edge portions;
an outer surface of the sidewall of the first shaft is a first radial distance from the first shaft long axis, the first radial distance being a maximum distance the outer surface of the sidewall of the first shaft extends from the first shaft long axis;
the middle edge portion includes a location with a second radial distance from the first shaft long axis, the second radial distance being a maximum distance the middle edge portion extends from the first shaft long axis;
the blade, when fully deployed, extends a third radial distance from the first shaft long axis, the third radial distance being a maximum distance the blade extends from the first shaft long axis when the blade is fully deployed;
the first, second, and third radial distances are orthogonal to the first shaft long axis;
the second radial distance is greater than the first radial distance and less than the third radial distance.

12. The apparatus of claim 1 comprising a dowel pin traversing an additional aperture included in the blade.

13. The apparatus of claim 1 wherein:
the raised edge includes a first lateral edge portion, a second lateral edge portion, and a middle edge portion between the first and second lateral edge portions; and
proximal-most locations of the first and second lateral edge portions contact the first shaft proximal to where a proximal-most location of the middle edge portion contacts the first shaft.

14. An apparatus comprising:
a first shaft including a first shaft proximal end, a first shaft distal end, and a first shaft long axis, wherein the first shaft distal end comprises a raised edge that extends away from the first shaft long axis;

a second shaft included within the first shaft;
a blade coupled to the second shaft;
wherein (a)(i) the raised edge is curvilinear, (a)(ii) the raised edge includes a first lateral edge portion, a second lateral edge portion, and a middle edge portion that couples the first and second lateral edge portions to each other; and (a)(iii) the first and second lateral edge portions are both proximal to the middle edge portion;
wherein (b)(i) the raised edge includes a thickness between first and second walls of the raised edge; (b)(ii) the thickness is parallel to the first shaft long axis; (b)(iii) the first wall of the raised edge is between the first shaft proximal end and the second wall of the raised edge; and
(b)(iv) the first wall of the raised edge is arranged to contact tissue when the raised edge contacts the tissue and the first shaft proximal end is moved proximally.

15. The apparatus of claim 14 wherein:
the first lateral edge portion extends a first radial distance from the first shaft long axis, the first radial distance being a maximum distance the first lateral edge portion extends from the first shaft long axis;
the second lateral edge portion extends a second radial distance from the first shaft long axis, the second radial distance being a maximum distance the second lateral edge portion extends from the first shaft long axis;
the middle edge portion extends a third radial distance from the first shaft long axis, the third radial distance being a maximum distance the middle edge portion extends from the first shaft long axis;
an outer surface of a sidewall of the first shaft is a fourth radial distance from the first shaft long axis, the fourth radial distance being a maximum distance the outer surface of the sidewall of the first shaft extends from the first shaft long axis;
the blade, when fully deployed, extends a fifth radial distance from the first shaft long axis, the fifth radial distance being a maximum distance the blade extends from the first shaft long axis when the blade is fully deployed;
the first, second, third, fourth and fifth radial distances are orthogonal to the first shaft long axis;
the third radial distance is greater than each of the first, second, and fourth radial distances; and
the third radial distance is less than the fifth radial distance.

16. The apparatus of claim 14 wherein:
the thickness is less than 0.03 inches;
at least one of the first lateral edge portion, the second lateral edge portion, or the middle edge portion includes a top exposed surface that projects at an acute angle that is greater than 20 degrees with respect to the first shaft long axis;
the acute angle and an obtuse angle are supplementary angles with one another; and
the obtuse angle is proximal to the acute angle.

17. The apparatus of claim 16 wherein:
the raised edge includes a pointed tip formed by a junction of the first and second walls of the raised edge;
an additional axis traverses the pointed tip and bisects a distance between the first and second walls of the raised edge;
the additional axis projects at an additional acute angle with respect to the first shaft long axis;
the additional acute angle is greater than 20 degrees;
the additional acute angle and an additional obtuse angle are supplementary angles with one another; and
the additional obtuse angle is proximal to the additional acute angle.

18. The apparatus of claim 14 wherein the first shaft distal end includes an arcuate surface that is curvilinear in first and second planes that are orthogonal to each other.

19. An apparatus comprising:
a shaft including a shaft proximal end, a shaft distal end, and a shaft long axis, wherein the shaft distal end comprises a raised edge that extends away from the shaft long axis;
a coupler included within the shaft;
a blade coupled to the coupler;
wherein (a)(i) the raised edge is curvilinear, (a)(ii) the raised edge includes a first lateral edge portion, a second lateral edge portion, and a middle edge portion that couples the first and second lateral edge portions to each other; and (a)(iii) the first and second lateral edge portions are both proximal to the middle edge portion;
wherein at least one of the first lateral edge portion, the second lateral edge portion, or the middle edge portion includes a top exposed surface that projects at an acute angle that is greater than 20 degrees with respect to the shaft long axis;
wherein the acute angle and an obtuse angle are supplementary angles with one another and the obtuse angle is proximal to the acute angle.

20. The apparatus of claim 19, wherein the first shaft distal end includes an arcuate surface that is curvilinear in first and second planes that are orthogonal to each other.

* * * * *

UNITED STATES PATENT AND TRADEMARK OFFICE
CERTIFICATE OF CORRECTION

PATENT NO. : 11,974,769 B2
APPLICATION NO. : 17/836514
DATED : May 7, 2024
INVENTOR(S) : Ira Lown It is certified that error appears in the above-identified patent and that said Letters Patent is hereby corrected as shown below:

In the Claims

Column 11:
Line 47, "E", should be --The--.

Signed and Sealed this
Fourth Day of June, 2024

Katherine Kelly Vidal
*Director of the United States Patent and Trademark Office*